United States Patent
Jiang et al.

(10) Patent No.: US 7,654,734 B2
(45) Date of Patent: Feb. 2, 2010

(54) METHODS AND DEVICES FOR EVALUATING THE THERMAL EXPOSURE OF A METAL ARTICLE

(75) Inventors: Liang Jiang, Schenectady, NY (US);
Lawrence Bernard Kool, Clifton Park, NY (US); Melvin Robert Jackson, Corea, ME (US); Canan Uslu Hardwicke, Greenville, SC (US); Ji-Cheng Zhao, Latham, NY (US); Ann Melinda Ritter, Niskayuna, NY (US); Ching-Pang Lee, Cincinnati, OH (US)

(73) Assignee: General Electric Company, Niskayuna, NY (US)

( * ) Notice: Subject to any disclaimer, the term of this patent is extended or adjusted under 35 U.S.C. 154(b) by 287 days.

(21) Appl. No.: 11/126,793

(22) Filed: May 10, 2005

(65) Prior Publication Data
US 2006/0256833 A1    Nov. 16, 2006

(51) Int. Cl.
*G01N 25/72*    (2006.01)
*G01N 17/00*    (2006.01)
*G01K 3/00*    (2006.01)
(52) U.S. Cl. .................. 374/5; 374/57; 374/7; 374/102
(58) Field of Classification Search .................. 374/137, 374/144, 5, 45, 57, 15, 4, 180, 7, 102; 324/750
See application file for complete search history.

(56) References Cited

U.S. PATENT DOCUMENTS

| | | | | |
|---|---|---|---|---|
| 1,327,341 A | * | 1/1920 | MacDonald et al. | 374/5 |
| 2,673,325 A | * | 3/1954 | Orr | 219/162 |
| 2,750,791 A | * | 6/1956 | Hanysz et al. | 374/7 |
| 3,258,957 A | * | 7/1966 | Smart | 374/5 |
| 3,555,879 A | * | 1/1971 | Schroeer et al | 374/5 |
| 3,667,032 A | * | 5/1972 | Summers, Jr. | 324/451 |

(Continued)

FOREIGN PATENT DOCUMENTS

EP    0944866    5/2001

(Continued)

OTHER PUBLICATIONS

JP 2001124763, Hino Takeshi et al., Method and System for Diagram Remainging Life of Gas Turbine High-Temperature Part, May 11, 2001.

(Continued)

*Primary Examiner*—Gail Verbitsky
*Assistant Examiner*—Mirellys Jagan
(74) *Attorney, Agent, or Firm*—Francis T. Coppa

(57) ABSTRACT

A method for evaluating the thermal exposure of a selected metal component which has been exposed to changing temperature conditions is described. The voltage distribution on a surface of the metal component, or on a metallic layer which lies over the component, is first obtained. The voltage distribution usually results from a compositional change in the metal component. The voltage distribution is then compared to a thermal exposure-voltage model which expresses voltage distribution as a function of exposure time and exposure temperature for a reference standard corresponding to the metal component. In this manner, the thermal exposure of the selected component can be obtained. A related device for evaluating the thermal exposure of a selected metal component is also described.

20 Claims, 1 Drawing Sheet

U.S. PATENT DOCUMENTS

| | | | | |
|---|---|---|---|---|
| 4,156,840 | A * | 5/1979 | Rowsey et al. | 324/451 |
| 4,320,344 | A * | 3/1982 | Nicholas | 324/451 |
| 4,556,328 | A | 12/1985 | Orpet | |
| 4,674,901 | A * | 6/1987 | Lorenz | 374/169 |
| 4,764,025 | A * | 8/1988 | Jensen | 374/144 |
| 4,797,006 | A | 1/1989 | Masom | |
| 4,902,139 | A * | 2/1990 | Adiutori | 374/137 |
| 4,923,308 | A | 5/1990 | Watanabe et al. | |
| 4,970,670 | A | 11/1990 | Twerdochlib | |
| 5,052,819 | A * | 10/1991 | Baratta | 374/43 |
| 5,094,544 | A * | 3/1992 | Ignatowicz | 374/126 |
| 5,203,632 | A | 4/1993 | Fisher et al. | |
| 5,217,305 | A * | 6/1993 | Yamakawa et al. | 374/45 |
| 5,261,747 | A * | 11/1993 | Deacutis et al. | 374/137 |
| 5,364,186 | A | 11/1994 | Wang et al. | |
| 5,748,317 | A * | 5/1998 | Maris et al. | 356/502 |
| 6,431,748 | B1 * | 8/2002 | Baratta | 374/45 |
| 6,491,425 | B1 * | 12/2002 | Hammiche et al. | 374/43 |
| 6,568,846 | B1 * | 5/2003 | Cote et al. | 374/5 |
| 6,599,416 | B2 * | 7/2003 | Kool et al. | 205/717 |
| 6,796,709 | B2 * | 9/2004 | Choi | 374/102 |
| 7,175,720 | B2 * | 2/2007 | Schnell et al. | 148/509 |
| 2003/0167616 | A1 * | 9/2003 | Harding et al. | 29/407.05 |
| 2004/0082069 | A1 | 4/2004 | Jiang et al. | |
| 2004/0120383 | A1 * | 6/2004 | Kennedy et al. | 374/57 |

FOREIGN PATENT DOCUMENTS

GB          2125556 A *  3/1984

OTHER PUBLICATIONS

"Alloy Thermo-Sorter for Nondestructive Testing (NDT)—ATS-6044T" Printed from Internet.

* cited by examiner

METHODS AND DEVICES FOR EVALUATING THE THERMAL EXPOSURE OF A METAL ARTICLE

BACKGROUND OF THE INVENTION

This invention generally relates to metal components. More specifically, the invention is directed to methods and devices for evaluating the thermal exposure of metal components which have been exposed to a variety of service conditions.

A variety of metal alloys are frequently used in industrial environments which include extreme operating conditions. For example, the alloys may be exposed to high temperatures (e.g., 500° C. or higher) for a long duration. Moreover, the alloys may be subjected to repeated temperature cycling, e.g., exposure to high temperatures, followed by cooling to room temperature, and then followed by rapid re-heating. As an example, gas turbine engines are often subjected to repeated thermal cycling during operation. Furthermore, the standard operating temperature of turbine engines continues to be increased, to achieve improved fuel efficiency. After gas turbine engine components are exposed to these conditions, they often undergo significant metallurgical changes, e.g., in chemistry or microstructure.

Monitoring the temperature of the turbine components can be extremely important for predicting engine failure, and for designing and optimizing the turbine engines. One technique for monitoring the temperature is sometimes referred to as "mapping", in which the average exposure temperature of the component (e.g., a blade) is recorded—during actual service, or by using test coupons under experimental conditions. Mapping of the temperature profile of a turbine component is very useful for evaluating turbine design; estimating metallurgical changes, and providing estimates as to the remaining life of the turbine component.

In general, many different techniques are available for estimating the temperature history of a component, e.g., a blade or other rotating member within a turbine engine. For example, the component can be physically sectioned after service, and evaluated with a number of devices and techniques, such as optical microscopy, scanning electron microscopy (SEM), X-ray diffraction, and transmission electron microscopy (TEM). The temperature profile can then be estimated from this evaluation. Documented time/temperature/characteristic feature relationships, similar to the well-known Larsen-Miller parameters developed for the testing of metal alloys, are useful for this purpose.

Non-destructive techniques for temperature evaluation have also been described in the art. For example, a method for evaluating the remaining life of a high-temperature turbine component is described by H. Takehisa et al, in JP-2001124763A2. According to this technique, parts formed from rhenium-containing nickel alloys are examined to determine particle size or the precipitation amount of a gamma prime phase for the alloy, after high-temperature exposure. It appears that the remaining life of the component is estimated by determining the time at which the degraded phase for a pre-determined precipitation amount is detected.

In U.S. Pat. No. 4,923,308 (Watanabe et al), a process is described, for determining the relative temperature distribution at a surface of a high-temperature component used in an oxygen-containing environment. In this process, a wheel or other test specimen is formed initially. The wheel is made of silicon carbide or silicon nitride, and is exposed to a temperature environment which simulates that of the component being evaluated. The wheel is then cut in the shape of a vane, and oxygen concentration is measured for the wheel surface. The oxygen concentration distribution is said to correlate to the surface temperature distribution, thereby providing an estimate as to the component's temperature history.

U.S. Pat. No. 4,970,670 (Twerdochlib) describes a system for monitoring the temperature of a plurality of turbine blade shroud segments. Each shroud contains some feature ("indicia") which is monitored by a sensor. In some embodiments, the sensor appears to sense eddy currents generated in each segment during movement of the shroud segment. A temperature sensor is responsive to changes in the temperature of the eddy current sensor. Input signals produced by the eddy currents are subjected to a correction mechanism, which in turn appears to provide data regarding the temperature history of the shroud segment.

Various conventional devices are also frequently used for the temperature-evaluation of metal components. Commercial examples are thermocouples, optical pyrometers, and black-body temperature sensors. Details and features for these types of instruments can be found in a wide variety of references.

The techniques discussed above for evaluating the temperature history of a component may be useful in a number of situations. However, most of those techniques have some notable disadvantages. For example, the technique in which a component is sectioned for examination is a destructive test which can be laborious and time-consuming. Furthermore, the conventional, temperature-measuring devices also have some drawbacks—especially when used in a harsh environment. For example, the accuracy of pyrometers can suffer because of "noise" caused by the passage of very hot particles through the component. Radiation pyrometers are also susceptible to interference from reflections and radiation originating from regions other than that which is under evaluation. Moreover, thermocouples, while being relatively inexpensive, are often too fragile for extended use in a harsh environment.

Some of the other non-destructive techniques mentioned above appear to require laborious procedures for temperature evaluation. Moreover, they may require a complex arrangement of sensors. The accuracy of some of these techniques may also be uncertain. For example, the process described above in U.S. Pat. No. 4,923,308 utilizes silicon-based wheels in place of the actual metal part being evaluated. Since the heat transfer characteristics of the silicon material may differ significantly from that of the metal component, the temperature measurement may not adequately correspond to the actual temperature exposure of the component.

It should thus be apparent that new techniques and systems for evaluating the thermal exposure of metal components would be of considerable interest in the art. The techniques should be non-destructive to the component being examined. They should also be accurate and relatively easy to carry out for a variety of metal substrates. Moreover, the techniques should be especially suitable for providing temperature profile measurements for superalloy components exposed to relatively high temperatures.

BRIEF DESCRIPTION OF THE INVENTION

One embodiment is directed to a method for evaluating the thermal exposure of a selected metal component which has been exposed to changing temperature conditions, comprising the following steps:

(a) determining the voltage distribution on a surface of the metal component, or on a metallic layer which lies over the component, said voltage distribution resulting from a compositional change in the metal component; and (b) comparing the voltage distribution to a thermal exposure-voltage model which expresses voltage distribution as a function of exposure time and exposure temperature for a reference standard corresponding to the metal component, so as to evaluate the thermal exposure of the selected component.

Another embodiment of this invention relates to a device for evaluating the thermal exposure of a selected metal component which has been exposed to changing temperature conditions. The device comprises the following elements:

(i) means for measuring the voltage distribution on a surface of the metal component, said voltage distribution resulting from a compositional change in the component; and (ii) means for comparing the voltage distribution to a thermal exposure-voltage model which expresses voltage distribution as a function of exposure time and exposure temperature for a reference standard corresponding to the metal component.

Further details regarding the various features of this invention are found in the remainder of the specification, and in the accompanying drawings.

DETAILED DESCRIPTION OF THE INVENTION

Figure 1:
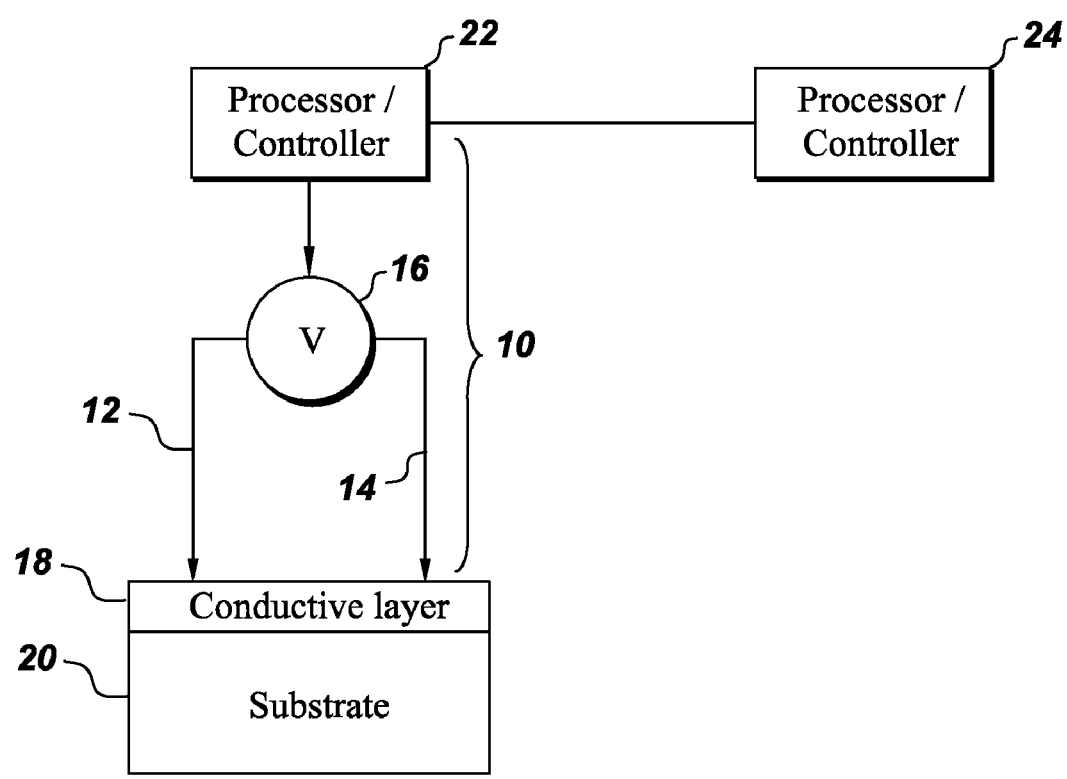
FIG. 1 is a simplified diagram of a device for evaluating the thermal exposure of a metal component according to some embodiments of the present invention.

As used herein, the term "thermal exposure" is meant to describe one or more heat-exposure parameters for a given metal component. Thus, the term may relate primarily to the approximate, average temperature to which the component has been subjected. The term may also refer to the approximate time for which the component has been exposed to a particular temperature, as well as the number of temperature cycles to which the component has been exposed. The parameters included within the profile will of course depend on the type and amount of information needed for analysis of the metal component.

The voltage distribution on the surface of the metal substrate results from a compositional change in the surface. The compositional change is usually (but not always) caused by oxidation of the substrate, or by the diffusion of substrate constituents, during high-temperature exposure. As an example, many metals and metal alloys form oxides when they are heated in an oxygen-containing atmosphere. Examples of the metals are nickel, cobalt, iron, titanium, and aluminum. Examples of the alloys are nickel-, iron-, and cobalt-based alloys, as well as titanium- and aluminum-based alloys. While this phenomenon often occurs naturally, it can also be induced by a variety of techniques, as further described below. (Moreover, this invention does not require the very high temperatures to which superalloys are typically exposed).

The diffusion phenomenon which occurs in metal components at high temperatures is understood to those skilled in the art. The phenomenon is especially prevalent in the case of high-temperature alloys which are provided with one or more protective coatings. Non-limiting examples of such materials are the commonly-used nickel-base superalloys, which usually include at least about 40 weight % nickel, as well as aluminum and at least one of tungsten, chromium, rhenium, tantalum, zirconium, cobalt, iron, yttrium, niobium, and the like. These superalloys are frequently exposed to temperatures above about 750° C. Therefore, they are often covered with a coating which protects them against oxidation and corrosion attack. Various types of coatings are used. One type is based on a material like MCrAl(X), where M is nickel, cobalt, or iron; and X is an element selected from the group consisting of Y, Ta, Si, Hf, Ti, Zr, B, C, and combinations thereof. Another type of protective coating is an aluminide material, such as nickel-aluminide or platinum-nickel-aluminide. A ceramic overcoat (e.g., a thermal barrier coating or "TBC") is often applied over the metallic coating. In that instance, the metallic coating usually functions as a bond layer between the TBC and the substrate.

The metallic protective coatings usually have relatively high aluminum content, as compared to the superalloy substrates. When the protective coatings and the substrate are exposed to a hot, oxidative, corrosive environment (as in the case of a gas turbine engine), various metallurgical processes occur. For example, a highly-adherent alumina ($Al_2O_3$) layer ("scale") usually forms on top of the protective coatings, resulting in the loss of aluminum from the coating during the oxidation process.

Moreover, at elevated temperatures, there is often a great deal of interdiffusion of elemental components between the coating and the substrate. The interdiffusion can change the chemical characteristics of each of these regions. In general, there is a tendency for the aluminum from the aluminum-rich protective layer to migrate inwardly toward the substrate. At the same time, traditional alloying elements in the substrate, such as cobalt, tungsten, chromium, rhenium, tantalum, molybdenum, and titanium, tend to migrate from the substrate into the coating. (These effects occur as a result of composition gradients between the substrate and the coating).

The compositional change required for the voltage distribution measurement can be induced by various techniques, even in the absence of traditional coatings used on the metal component. For example, a metal coating which is not readily oxidized could be applied directly over a test specimen of the component, prior to subjecting the specimen to a heat treatment. Such a coating would promote diffusion of elements from the underlying substrate, but would itself not be substantially consumed. Non-limiting examples of such materials are precious metals (noble metals) such as gold, silver, rhodium, and the like. The coating should be compatible with the particular substrate, e.g., a coating which does not readily form low-melting intermetallic compositions with the substrate. In the case of a nickel-based substrate, coatings which comprise rhodium or platinum are often preferred.

The voltage distribution which results from the compositional changes in a metal component can be detected by various techniques. Some of these techniques rely in part on an operational principle which is often referred to as the "Seebeck Effect" or "Seebeck Principle". This principle generally holds that when two dissimilar metals (e.g., metal wires) are joined to form a junction, and the opposite ends are also joined to form another junction, and one junction is heated, a predictable voltage will be generated between the junctions. This voltage relates to the difference in temperature between the junctions (e.g., a measuring junction and a reference junction). A thermocouple is a good example of a device which exploits this principle. Thermocouples are described widely. Illustrative sources include "The Art of Electronics", by P. Horowitz et al, Cambridge University Press, 1980, (pp. 591-608); and "The Encyclopedia Americana—International Edition", Grolier, Inc., Volume 26 (1981) (pp. 645, 657-658). (It should be understood that electrical parameters other than voltage might be measured in this technique. Non-limiting examples include electrical current, resistance, or resistivity. While the voltage measurement is preferred, the term "voltage" as used herein is meant to embrace those other electrical parameters as well).

In the present instance, devices which rely on the Seebeck Effect to identify metal alloys are particularly useful for measuring the voltage distribution on the surface of the metal component. One such device is the Alloy ThermoSorter™, model ATS-6044T, which is available from Walker Scientific, Inc., Worcester, Mass. This device uses a dual-tipped probe, which, in effect, serves as both a measuring junction and a reference junction. In other words, one tip of the probe is heated to a pre-selected temperature, while the other tip remains at ambient temperature. When the probe is placed on the alloy to be identified, an electric circuit through the alloy is completed, and a signal is generated. This signal corresponds to the voltage distribution (usually a single numerical value, in micro-volts) generated between the two junctions, which can also be referred to, in this context, as the electromotive force (EMF).

Thus, each alloy composition possesses a characteristic EMF value. (As described above, some of the high-temperature components include ceramic overcoats over the metallic protective coatings. Since the ceramic overcoats are generally non-conductive, portions of the overcoats may have to be removed, so as to allow an appropriate connection between the voltage-detection device and the metallic layer). Other details regarding the operation of the Alloy ThermoSorter can be found on an Internet web-site: http://www.walkerscientific.com. At least 6 pages relate to the ThermoSorter (e.g., http://www.walkerscientific.com/Walker/NDT/thermosorter.html).

The voltage distribution (EMF) can then be compared to a thermal exposure-voltage model. The term "model" should be construed broadly here. It includes any type of expression (electronic or otherwise) of voltage distribution as a function of exposure time and exposure temperature. The model is usually based on a reference standard which corresponds to the metal component. Such a model can readily be formulated, experimentally. For example, one can first determine the EMF for a number of samples which initially have a composition substantially identical to that of the metal component, but which are then purposefully treated in some way to change the composition.

As one illustration, a set of metal samples which are coated could each be subjected to a particular heat treatment. Each sample is exposed to a different combination of temperature and time. In each case, the temperature-time regimen is sufficient to cause a change in the composition of the sample, e.g., by oxidation or diffusion related to the presence of the coating, as described previously.

Any device similar in function to the ThermoSorter could be used to measure the EMF which results from the compositional change for each sample. The thermal exposure-voltage model could then be assembled from the collection of these EMF values, each corresponding to a specific temperature-time regimen. If the time of temperature-exposure for the selected metal component is known, reference to the model will provide the temperature to which the component has been exposed. Conversely, if the temperature to which the selected component has been exposed is known, reference to the model will provide the time of exposure.

It should be noted that the thermal exposure-voltage model could be based on compositional changes for a variety of elements or compounds in the metal component. For example, as discussed above, various alloying elements in superalloy substrates, such as cobalt, tungsten, chromium, and rhenium, tend to migrate into the coating at elevated temperatures. Thus, the changing concentration of one or more of these elements due to high-temperature exposure could also be examined in test specimens, to prepare the model.

Moreover, those skilled in the art understand that this process can be carried out with the aid of any type of computer processor. For example, the thermal exposure-voltage model can be generated (e.g., in graphical or table form) with appropriate software and hardware well-known to those in the art. Furthermore, conventional computer programs for regression analysis can automatically "fit" the EMF values for a selected component to the thermal exposure-voltage model, in order to obtain the most accurate thermal exposure evaluation.

The process described herein for evaluating thermal exposure is preferably carried out in the two primary steps described above. However, in some embodiments, an additional, intermediate step might be incorporated into the process, utilizing the compositional change in the metal component. For example, the voltage distribution obtained in the first step can be compared to a composition-voltage model which expresses the composition of the metal surface (or of a metallic layer thereon), as a function of voltage distribution. Instruments such as the Walker ThermoSorter generally function in this manner, utilizing alloy sample/coupons of known identity and known EMF values. The resulting composition can then be compared to a composition-temperature model which expresses the composition as a function of thermal exposure. Such a model can be obtained by known techniques, e.g., based on data for a number of test samples which express a compositional change (like aluminum concentration) under a variety of time and temperature-exposure conditions. The desired evaluation of thermal exposure for a given sample can thus be obtained.

Furthermore, the remaining service-life of a metal component can be predicted according to embodiments of this invention. For example, the thermal exposure-voltage model can include indicator limits as to when component failure is likely to occur. These indicator limits would be based on experimental data and/or other sources, such as the Larsen-Miller parameters.

A non-limiting example can be provided, for the case of the NiCrAlY-coated superalloy substrate discussed previously, after high-temperature exposure which results in aluminum diffusion, e.g., aluminum-loss from the substrate. Previously-obtained data might indicate that exposure of the component above a certain temperature for a certain time period (or number of cycles) can result in a surface-aluminum concentration which is indicative of potential component failure. The process described herein provides an indication of the thermal exposure for a particular component, and thereby allows an estimate as to the additional time (or number of additional cycles) to which the component can be subjected, before it should be discarded or repaired.

The time period determined in the thermal exposure evaluation can be expressed in terms of temperature cycles. Those skilled in the art understand that a temperature cycle usually involves first raising the temperature of the metal component from about ambient temperature to an elevated temperature (often about ½ of the metal's melting point). The component is then held at that temperature for a pre-selected time, and then cooled down to ambient temperature. Thus, if the entire cycle (heating, holding at the elevated temperature, and cooling down) was 4 hours in length, an exposure time of 100 hours for the metal component would be equal to 25 cycles.

The process described herein can be used for mapping the thermal exposure of a metal component. For example, the voltage distribution (EMF) can be determined for two or more locations on the surface of the component. Each of these EMF values can be converted to a corresponding thermal exposure parameter, i.e., exposure time (or cycles), or exposure temperature. In this manner, the thermal exposure of different sections of the component can be readily determined. That type of information can be extremely important in the case of high temperature components. For example, the specific, average heat exposure for particular locations on a turbine blade may be critical for predicting the service life of the blade, and for designing new blades.

Another embodiment of this invention is directed to a device for evaluating the thermal exposure of a metal component, i.e., one which has been exposed to changing temperature conditions. The device is generally depicted in FIG. 1, in simplified form. It comprises means 10 for measuring the voltage distribution (EMF) on a surface of the component.

As described above, any device which is capable of measuring voltage distribution on a metal alloy or a coated metal alloy, through application of the Seebeck Effect, is suitable for this purpose. In this non-limiting illustration, the device comprises an EMF measurement apparatus 10. Apparatus 10 includes a conductive sensing probe 12, which is maintained at a constant, elevated temperature by a calibration mechanism within the device. (The temperature is usually in the range of about 100° C.-250° C.). The apparatus further includes reference probe 14, which remains at ambient temperature. Each of the probes 12 and 14 is connected to an electrical measuring mechanism 16. (In the terminology used for the commercial Walker ThermoSorter, probes 12 and 14 could alternatively be referred to as "tips" which extend from a single "probe"). Depending on the particular features of the overall device, measuring mechanism 16 can measure current, voltage, or some other electrical value. Usually, mechanism 16 is one which measures voltage, e.g., a voltmeter. Apparatus 10 further comprises means 22 for processing readings from the probe. Means 22 is usually in the form of a conventional processor/controller. Processor/controller 22 can be directly attached to the other components of the EMF-measuring system, or it can be a separate unit. An example of an integrated device is the Alloy ThermoSorter discussed previously. Moreover, the apparatus also comprises an appropriate power supply (not shown), e.g., an AC/DC or battery supply, or a combination thereof.

As shown in FIG. 1, each of the probes 12, 14 can be placed in contact with a conductive layer 18 (in effect, forming the "junctions" described herein, upon contact). As described previously, layer 18 is often a metallic-based protective layer for a substrate. For example, layer 18 can be an MCrAlX layer or an aluminide-type layer, applied over metal substrate 20, e.g., a superalloy material. (As also explained above, conductive layer 18 need not be present for the operation of apparatus 10).

The overall device further comprises means for comparing the voltage distribution (EMF) to the thermal exposure-voltage model. As described previously, any instrument which can automatically receive the EMF measurements and compare them (e.g., by computer processing) with EMF measurements for one or more reference standards would be suitable for this purpose. The comparison allows the particular temperature value or time value corresponding to the EMF measurement to be obtained. As shown in FIG. 1, means for comparing EMF to the thermal exposure-voltage model is usually in the form of a conventional processor/controller 24. Processor/controller 24 can be integrated into EMF measurement apparatus 10 (e.g., a single processor/controller could perform the functions of both elements 22 and 24), or it can be a separate unit.

Those skilled in the art are familiar with techniques and mechanisms (both software and hardware) for integrating measurement apparatus 10 to processor/controller 24. Thus, EMF values obtained with the apparatus can be automatically processed to provide the desired time or temperature values for a metal component being examined. For example, the EMT data obtained for the particular component being examined can be input into processor/controller 24, using conventional software programs suited for this purpose.

Those skilled in the art understand that additional features can be added to the device described herein. As a non-limiting example, various calibration programs or algorithms can be incorporated into the EMF-measurement instrument, when the latter is computer based. The calibration programs can account for many variables, e.g., temperature-reading fluctuations and the like. Moreover, the computer/processors described above can include regression analysis programs for curve-fitting, as described previously. The computer/processors can also be adapted to simultaneously process a set of data corresponding to multiple EMF readings in a temperature-mapping process, as discussed above.

EXAMPLES

The example which follows is illustrative, and should not be construed to be any sort of limitation on the scope of the claimed invention.

Two metal plates were formed, each being about 2 inches×2 inches in size (5.1 cm×5.1 cm), with a thickness of about 4 mils (0.01 cm). One plate was formed of substantially pure rhodium, while the other plate was formed of substantially pure platinum. (These metals were selected because they do not oxidize readily). The plates were placed together, face-to-face, and the edges were welded together by electron beam welding. The plates were then pressed together, using a HIP (hot isostatic pressing) technique, at 1200° C. under 30 ksi pressure, for about 1 hour.

The HIP technique resulted in some interdiffusion between the two metals. A number of individual samples were then cut from the plate structure, each being 0.5 inch×0.5 inch in size (1.27 cm×1.27 cm). Each sample was then heated in an air furnace, according to a specific heating schedule, as shown in Table 1 (below), which resulted in a compositional change.

After being cooled to room temperature, the EMF for each sample was determined, using an Alloy ThermoSorter (model ATS-6044T). Three different readings were taken for each sample (on the rhodium side of the sample), and the EMT values were averaged. The results are shown in the table:

TABLE 1

| Temperature ↓ | 24 Hours | 100 Hours | 204 Hours | 501 Hours |
|---|---|---|---|---|
| 2200° F./1204° C. | 72[a][b] | 72 | 65 | 44 |
| 2000° F./1093° C. | 77 | 73 | 69 | 63 |

[a]All values are EMF values, in micro-volts
[b]The standard deviations (Std. Dev.) for the EMF values were as follows:

| | Std. Dev. | | | |
|---|---|---|---|---|
| | 24 hrs | 100 hrs | 204 hrs | 501 hrs |
| 2200° F./1204° C. | 1.7 | 4.2 | 2.1 | 2.9 |
| 2000° F./1093° C. | 2.1 | 2.6 | 1.2 | 1.2 |

Table 1 is an example of a thermal exposure-voltage model, described previously. The model allows one to determine either the time of thermal exposure, or the exposure temperature, for a selected metal component being examined. (The metal component would have a platinum-rhodium composition, in this instance). As an example (with reference to Table 1), an EMF value of 44 might be obtained for a component, using a ThermoSorter-type device. If the component were known to be in service for about 501 hours, one could estimate that its average temperature-exposure was about 1204° C. In a similar fashion, if the component were known to be in service at a temperature of about 1204° C., then the EMF reading of 44 would indicate that the component was in service for about 501 hours.

As described previously, a thermal exposure-voltage model like that of Table 1 can be constructed for various types of metal substrates or metal components. (For example, the substrate would take the place of one of the plates used in this example, while a metallic coating over the substrate would serve as the second plate). As mentioned previously, the component is often a portion of a turbine, e.g., a gas turbine engine. Non-limiting examples of such components include turbine buckets, nozzles, blades, rotors, vanes, stators, shrouds, and combustors.

Moreover, while Table 1 consisted of 11 data points, a table could be constructed with a much greater number of data points. In other words, EMF readings could be taken for a large number of samples over many different temperature/time schedules. In this manner, the precision of the process could be greatly increased, if necessary. The use of one or more computer processors (discussed above) allows one to readily evaluate large amounts of the thermal data, to quickly obtain the desired thermal exposure values.

Persons of ordinary skill in the art will recognize the utility of variations and additions that are possible in both the apparatus and method of use disclosed herein, without departing from the scope of this invention. Accordingly, it is understood that the scope is to be limited only by the appended claims.

What is claimed is:

1. A method for evaluating the thermal exposure of a selected metal component which has been exposed to changing temperature conditions, comprising the following steps:
   (a) determining the voltage distribution on a surface of the metal component, or on a protective metallic layer which lies over the component, said voltage distribution resulting from a compositional change in the metal component; and
   (b) comparing the voltage distribution to a thermal exposure-voltage model which expresses voltage distribution as a function of exposure time and exposure temperature for a reference standard corresponding to the metal component, so as to evaluate the thermal exposure of the selected component.

2. The method of claim 1, wherein the thermal exposure evaluation comprises an approximate, average temperature value over a selected time period.

3. The method of claim 1, wherein the voltage distribution is determined by an electrical measurement device which comprises a sensing probe and a reference probe, both in contact with the component surface, wherein heating of the sensing probe while the reference probe is maintained at ambient temperature results in the development of a measurable voltage.

4. The method of claim 1, wherein the compositional change in the metal component is caused by migration of one or more elements from the component to a layer which overlies the component.

5. The method of claim 1, wherein the compositional change is caused by oxidation of the metal component.

6. The method of claim 1, further comprising the step of determining the remaining service life of the metal component, by calculating the difference between a value corresponding to the thermal exposure obtained for the components and a predicted thermal exposure value for a standard metal component of similar composition, wherein the predicted thermal exposure value corresponds to the projected service life of the standard metal component.

7. The method of claim 1, wherein the thermal exposure evaluation comprises a time period of exposure at a selected temperature.

8. The method of claim 7, wherein the time period is expressed in temperature cycles.

9. The method of claim 1, wherein the thermal exposure-voltage model is obtained from a set of test specimens having known voltage distribution (EMF) characteristics, wherein the test specimens are formed of the same type of material as the selected metal component.

10. The method of claim 9, wherein each test specimen is subjected to a different time/temperature schedule for thermal exposure, and the corresponding EMF value for each specimen is recorded.

11. The method of claim 1, wherein the metal component comprises aluminum and at least one of nickel or cobalt; and an aluminum-containing coating lies over the component.

12. The method of claim 11, wherein the component is a nickel-based superalloy, and the overlying coating comprises at least one composition selected from the group consisting of MCrAlX, aluminide, platinum-aluminide; nickel-aluminide; and platinum-nickel-aluminide, wherein M is selected from the group consisting of Fe, Ni, Co, and mixtures of any of the foregoing; and X is selected from the group consisting of Y, Ta, Si, Hf, Ti, Zr, B, C, and combinations thereof.

13. A method for evaluating the thermal exposure of a selected superalloy turbine component which has been exposed to high-temperature conditions, comprising the following steps:
   (a) determining the voltage distribution on a surface of the turbine component, or on a protective layer which lies over the component, said voltage distribution resulting from a compositional change in the superalloy component; and
   (b) comparing the voltage distribution to a thermal exposure-voltage model which expresses voltage distribution as a function of exposure time and exposure temperature for a reference standard corresponding to the turbine component, so as to evaluate the thermal exposure of the selected component.

14. The method of claim 13, wherein the turbine component comprises a nickel-based superalloy, and the protective layer comprises a material selected from the group consisting of MCrAlX compositions, aluminide compositions, platinum-aluminide compositions, nickel-aluminide compositions; and platinum-nickel-aluminide compositions, wherein M is selected from the group consisting of Fe, Ni, Co. and mixtures of any of the foregoing; and X is selected from the group consisting of Y, Ta, Si, Hf, Ti, Zr, B, C, and combinations thereof.

15. The method of claim 14, wherein the compositional change results from oxidation of the protective layer, or from migration of elements from the superalloy into the protective layer.

16. A device for evaluating the thermal exposure of a selected metal component which has been exposed to changing temperature conditions, comprising:

(i) means for measuring the voltage distribution on a surface of the metal component, said voltage distribution resulting from a compositional change in the component; and (ii) means for comparing the voltage distribution to a thermal exposure-voltage model which expresses voltage distribution as a function of exposure time and exposure temperature for a reference standard corresponding to the metal component.

17. The device of claim 16, wherein element (i) comprises an EMF-measurement device which functions according to the Seebeck Principle.

18. The device of claim 16, wherein element (i) comprises an EMF-measurement device which itself comprises a sensing probe which can be maintained at a constant, elevated temperature, and a reference probe; wherein both probes are connected in circuit with an electrical measuring mechanism, and both probes are capable of simultaneously contacting the component surface;

wherein heating of the sensing probe while the reference probe is maintained at ambient temperature during the time the probes contact the component surface results in the development of a measurable voltage (EMF) which is characteristic of the component.

19. The device of claim 16, wherein component (ii) comprises at least one computer processor and associated computer software.

20. A method of temperature-mapping a selected metal component which has been exposed to changing temperature conditions, comprising the following steps:

(a) determining the voltage distribution at a selected location on a surface of the metal component, or at a selected location on a protective metallic layer which lies over the component, said voltage distribution resulting from a compositional change in the metal component;

(b) comparing the voltage distribution to a thermal exposure-voltage model which expresses voltage distribution as a function of exposure time and exposure temperature for a reference standard corresponding to the metal component, so as to evaluate the thermal exposure of the selected component at the selected location; and (c) repeating steps (a) and (b) for at least one additional, selected location, so as to provide a map of thermal exposure values for the metal component.

* * * * *

UNITED STATES PATENT AND TRADEMARK OFFICE
CERTIFICATE OF CORRECTION

PATENT NO. : 7,654,734 B2  Page 1 of 1
APPLICATION NO. : 11/126793
DATED : February 2, 2010
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 460 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,654,734 B2 | Page 1 of 1 |
| APPLICATION NO. | : 11/126793 | |
| DATED | : February 2, 2010 | |
| INVENTOR(S) | : Jiang et al. | |

It is certified that error appears in the above-identified patent and that said Letters Patent is hereby corrected as shown below:

In Column 8, Line 10, delete "EMT" and insert -- EMF --, therefor.

In Column 8, Line 50, delete "EMT" and insert -- EMF --, therefor.

In Column 10, Lines 6-7, in Claim 6, delete "components" and insert -- component, --, therefor.

In Column 10, Line 54, in Claim 14, delete "MCrAIX" and insert -- MCrAlX --, therefor.

In Column 10, Line 57, in Claim 14, delete "Co." and insert -- Co, --, therefor.

Signed and Sealed this
Twenty-fifth Day of January, 2011

David J. Kappos
*Director of the United States Patent and Trademark Office*